United States Patent
Dinh et al.

(10) Patent No.: US 8,962,863 B2
(45) Date of Patent: Feb. 24, 2015

(54) PROCESS FOR THE SYNTHESIS OF SUBSTITUTED GAMMA LACTAMS

(71) Applicant: Allergan, Inc., Irvine, CA (US)

(72) Inventors: Danny T. Dinh, Costa Mesa, CA (US); Michael E. Garst, Newport Beach, CA (US); David W. Old, Irvine, CA (US); Elizabeth T. Syage, Huntington Beach, CA (US); Boris Gorin, Oakville, CA (US); Christopher M. Lanthier, Burlington, CA (US); Jan Oudenes, Aurora, CA (US)

(73) Assignee: Allergan, Inc., Irvine, CA (US)

( * ) Notice: Subject to any disclaimer, the term of this patent is extended or adjusted under 35 U.S.C. 154(b) by 0 days.

(21) Appl. No.: 13/970,694

(22) Filed: Aug. 20, 2013

(65) Prior Publication Data

US 2014/0058117 A1    Feb. 27, 2014

Related U.S. Application Data

(60) Provisional application No. 61/691,559, filed on Aug. 21, 2012.

(51) Int. Cl.
*C07D 417/12*   (2006.01)
*A61K 31/4025*  (2006.01)
*C07D 409/12*   (2006.01)
*H04N 5/232*    (2006.01)

(52) U.S. Cl.
CPC .......... *C07D 409/12* (2013.01); *H04N 5/23229* (2013.01); *H04N 5/23293* (2013.01)
USPC .......................................... 548/527; 514/422

(58) Field of Classification Search
None
See application file for complete search history.

(56) References Cited

U.S. PATENT DOCUMENTS 7,482,475 B2 *   1/2009   Old et al. ................. 548/545
2008/0269498 A1  10/2008  Old

FOREIGN PATENT DOCUMENTS

WO    2005-061449    7/2005
WO    2008-021975    2/2008
WO    2009-132088   10/2009

OTHER PUBLICATIONS

Patent Cooperation Treaty, Notification of Transmittal of the International Search Report and the Written Opinion of the International Searching Authority, or the Declaration, Form PCT/ISA/220, Int. App. No. PCT/US2013/055685, Oct. 15, 2013.

* cited by examiner

*Primary Examiner* — Michael Barker
(74) *Attorney, Agent, or Firm* — Jonathan Y. Bass

(57) ABSTRACT

The present invention provides synthetic processes for the preparation of a variety of well-defined substituted gamma lactams. The compounds that can be prepared by the process of the invention are useful for treating a variety of conditions. In some embodiments of the invention, the compounds are useful for treating ocular disorders, such as, for example, glaucoma, lowering of elevated intraocular pressure, and the like. In other embodiments, the compounds are useful for treating irritable bowel disease. In further embodiments, the compounds are useful in promoting hair growth. In still further embodiments, the compounds are useful in promoting wound healing, scar reduction, and the like.

11 Claims, No Drawings

PROCESS FOR THE SYNTHESIS OF SUBSTITUTED GAMMA LACTAMS

CROSS-REFERENCE TO RELATED APPLICATION

This application claims the benefit of U.S. Provisional Ser. No. 61/691,559 filed on Aug. 21, 2012, which is incorporated by reference herein.

FIELD OF THE INVENTION

This invention relates generally to the synthesis of substituted gamma lactams, which are useful as pharmaceutical compounds, e.g. as medicinal compounds useful for treating glaucoma and/or lower elevated intraocular pressure.

SUMMARY OF THE INVENTION

The present invention provides synthetic processes for the preparation of a variety of well-defined substituted gamma lactams. The compounds that can be prepared by the process of the invention are useful for treating a variety of conditions. In some embodiments of the invention, the compounds are useful for treating ocular disorders, such, for example, glaucoma, lowering of elevated intraocular pressure, and the like. In other embodiments, the compounds are useful for treating irritable bowel disease. In further embodiments, the compounds are useful in promoting hair growth. In still further embodiments, the compounds are useful in promoting wound healing, scar reduction, and the like.

In one embodiment of the invention there are provided processes for preparing a compound having the general structure (1)

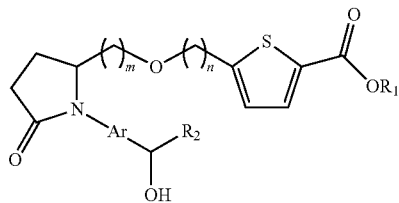

(1)

wherein:

$R_1$ is H, $C_1$-$C_6$ alkyl, or hydroxyethyl;
$R_2$ is $C_1$-$C_{10}$ alkyl;
Ar is $C_5$-$C_{10}$ arylene or heteroarylene; and
m and n are each independently 1-6.

Such processes can be performed, for example by:
a) reacting compound (2)

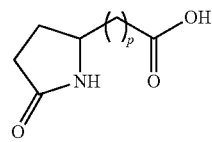

(2)

wherein p is 0 to 5;
with an alcohol having the structure $R_1$—OH under suitable esterifying conditions to provide compound (3)

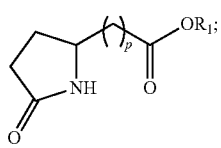

(3)

(b) coupling compound (3) with compound (5)

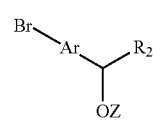

(5)

wherein Z is a protecting group,
under suitable conditions to provide compound (6)

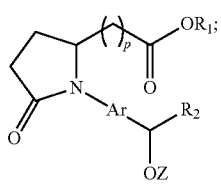

(6)

(c) subjecting compound (6) to sufficient reducing conditions to provide compound (7)

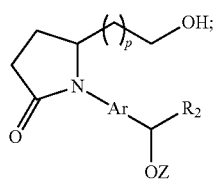

(7)

(d) coupling compound (7) with compound (8)

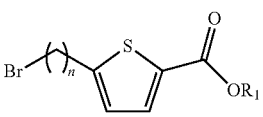

(8)

under suitable conditions to provide compound (9)

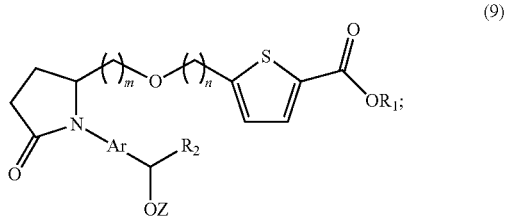

and
(e) subjecting compound (9) to acidifying conditions,
thereby providing a compound of general structure (1).

DETAILED DESCRIPTION OF THE INVENTION

It is to be understood that both the foregoing general description and the following detailed description are exemplary and explanatory only and are not restrictive of the invention claimed. As used herein, the use of the singular includes the plural unless specifically stated otherwise. As used herein, "or" means "and/or" unless stated otherwise. Furthermore, use of the term "including" as well as other forms, such as "includes," and "included," is not limiting. The section headings used herein are for organizational purposes only and are not to be construed as limiting the subject matter described.

Unless specific definitions are provided, the nomenclatures utilized in connection with, and the laboratory procedures and techniques of analytical chemistry, synthetic organic and inorganic chemistry described herein are those known in the art. Standard chemical symbols are used interchangeably with the full names represented by such symbols. Thus, for example, the terms "hydrogen" and "H" are understood to have identical meaning. Standard techniques may be used for chemical syntheses, chemical analyses, and formulation.

As used herein, "alkyl" refers to straight or branched chain hydrocarbyl groups having from 1 up to about 100 carbon atoms. Whenever it appears herein, a numerical range, such as "1 to 100" or "$C_1$-$C_{100}$", refers to each integer in the given range; e.g., "$C_1$-$C_{100}$ alkyl" means that an alkyl group may comprise only 1 carbon atom, 2 carbon atoms, 3 carbon atoms, etc., up to and including 100 carbon atoms, although the term "alkyl" also includes instances where no numerical range of carbon atoms is designated. "Substituted alkyl" refers to alkyl moieties bearing substituents including alkyl, alkenyl, alkynyl, hydroxy, oxo, alkoxy, mercapto, cycloalkyl, substituted cycloalkyl, heterocyclic, substituted heterocyclic, aryl, substituted aryl, heteroaryl, substituted heteroaryl, aryloxy, substituted aryloxy, halogen, haloalkyl, cyano, nitro, nitrone, amino, lower alkylamino, lower alkyldiamino, amido, azido, —C(O)H, —C(O)$R_7$, —CH$_2$O$R_7$, —C(O)—, —C(O)—, —S—, —S(O)$_2$, —OC(O)—O—, wherein $R_7$ is H or lower alkyl, acyl, oxyacyl, carboxyl, carbamate, sulfonyl, sulfonamide, sulfuryl, and the like. As used herein, "lower alkyl" refers to alkyl moieties having from 1 to about 6 carbon atoms.

As used herein, "alkenyl" refers to straight or branched chain hydrocarbyl groups having at least one carbon-carbon double bond, and having in the range of about 2 up to about 100 carbon atoms, and "substituted alkenyl" refers to alkenyl groups further bearing one or more substituents as set forth above. As used herein, "lower alkenyl" refers to alkenyl moieties having from 2 to about 6 carbon atoms.

As used herein, "alkynyl" refers to straight or branched chain hydrocarbyl groups having at least one carbon-carbon triple bond, and having in the range of about 2 up to about 100 carbon atoms, and "substituted alkynyl" refers to alkynyl groups further bearing one or more substituents as set forth above. As used herein, "lower alkynyl" refers to alkynyl moieties having from 2 to about 6 carbon atoms.

As used herein, "cycloalkyl" refers to cyclic (i.e., ring-containing) alkyl moieties typically containing in the range of about 3 up to about 8 carbon atoms, and "substituted cycloalkyl" refers to cycloalkyl groups further bearing one or more substituents as set forth above.

As used herein, "aryl" refers to aromatic groups having in the range of 5 up to 14 carbon atoms and "substituted aryl" refers to aryl groups further bearing one or more substituents as set forth above.

As used herein, "heteroaryl" refers to aromatic moieties containing one or more heteroatoms (e.g., N, O, S, or the like) as part of the ring structure and having in the range of 5 up to 14 total atoms in the ring structure (i.e., carbon atoms and heteroatoms). "Substituted heterocyclic" refers to heterocyclic groups further bearing one or more substituents as set forth above.

As used herein, "heterocyclic" refers to non-aromatic cyclic (i.e., ring-containing) groups containing one or more heteroatoms (e.g., N, O, S, or the like) as part of the ring structure, and having in the range of 3 up to 14 carbon atoms and "substituted heterocyclic" refers to heterocyclic groups further bearing one or more substituents as set forth above.

As used herein, "halogen" or "halide" refers to fluoride, chloride, bromide or iodide. "Fluoride, chloride, bromide or iodide" may also be referred to as "fluoro, chloro, bromo, or iodo".

As used herein "arylene" refers to an aryl ring or ring system which connects two other parts of a molecule, i.e. the two parts are bonded to the ring in two distinct ring positions. "Heteroarylene" refers to a heteroaryl ring or ring system ring or which connects two other parts of a molecule. Arylene or heteroarylene may be substituted or unsubstituted. Unsubstituted arylene or heteroarylene has no substituents other than the two parts of the molecule it connects. Substituted arylene or heteroarylene has substituents in addition to the two parts of the molecule it connects.

The invention provides processes that can be used to prepare pharmaceutically useful substituted gamma lactams. Such processes can be performed, for example by:
a) reacting compound (2)

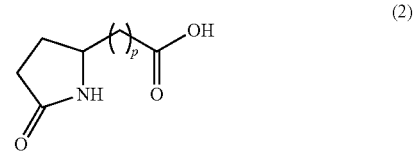

wherein p is 0 to 5;
with an alcohol having the structure $R_1$—OH under suitable esterifying conditions to provide compound (3)

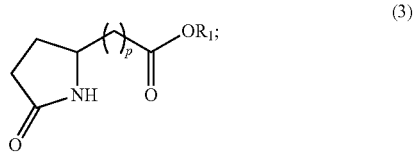

(b) coupling compound (3) with compound (5)

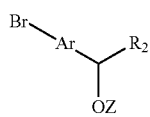
(5)

wherein Z is a protecting group,
under suitable conditions to provide compound (6)

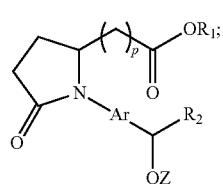
(6)

(c) subjecting compound (6) to sufficient reducing conditions to provide compound (7)

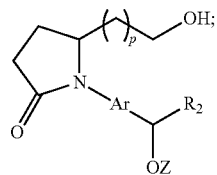
(7)

(d) coupling compound (7) with compound (8)

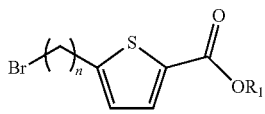
(8)

under suitable conditions to provide compound (9)

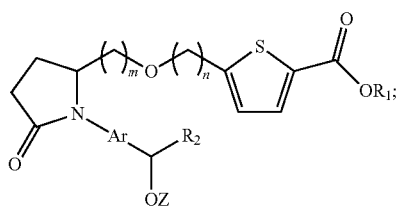
(9)

and
(e) subjecting compound (9) to acidifying conditions,
thereby providing a compound of general structure (1).

In some embodiments of the invention, Ar is phenylene or naphthylene. In certain embodiments, Ar is phenylene.

In some embodiments, $R_1$ is $C_3$ alkyl. In certain embodiments, $R_1$ is isopropyl.

In some embodiments, $R_2$ is linear $C_5$ alkyl.

In other embodiments of the invention, m and n are 1.

In some embodiments of the invention, the protecting group "Z" is $R_3R_4R_5Si$, wherein $R_3$, $R_4$, and $R_5$ are each independently $C_1$-$C_4$ straight or branched chain alkyl.

In some embodiments of the invention, coupling step (c) is performed in the presence of a metal halide catalyst. A wide range of metal halide catalysts are contemplated for use in the practice of the invention and are well known to those skilled in the art. In some embodiments, the metal halide catalyst is a copper halide. In certain embodiments, the metal halide catalyst is CuI.

An exemplary compound prepared by the synthetic process of the invention has the structure set forth below:

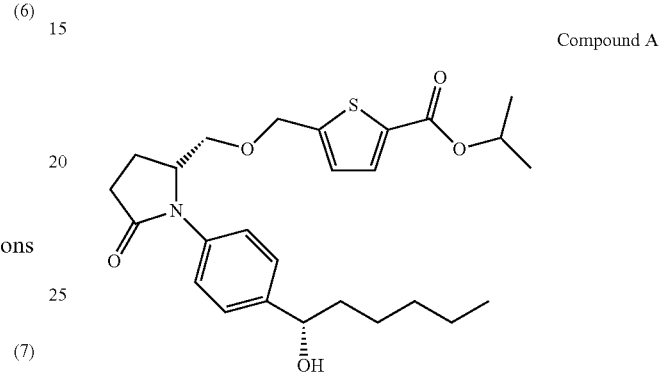
Compound A

The process described in Schemes 1-3 below may be altered according to reaction size or geometry of the equipment. Reaction times, temperatures and quantities of reagents indicated may be varied within reasonable limits as experience indicates to increase process efficiency without adversely affecting product characteristics. All reactions were carried out under inert atmosphere in suitable reactors equipped with appropriate stirring and temperature controls.

An exemplary synthetic outline is set forth below in Scheme 1, wherein Intermediate A is prepared.

Scheme 1

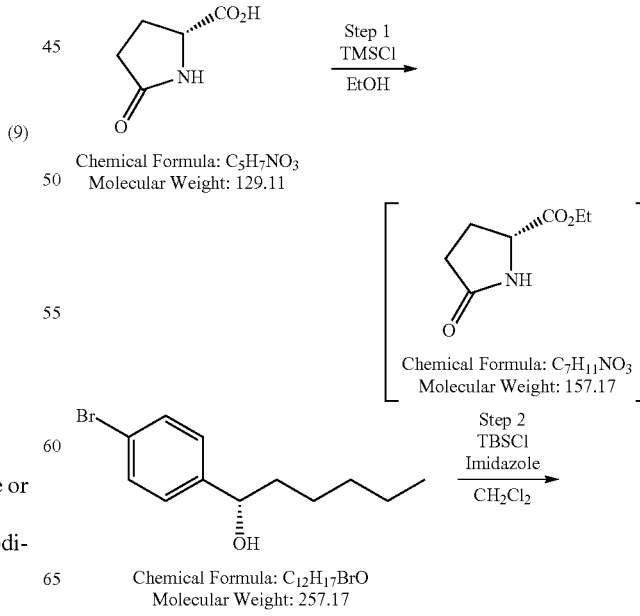

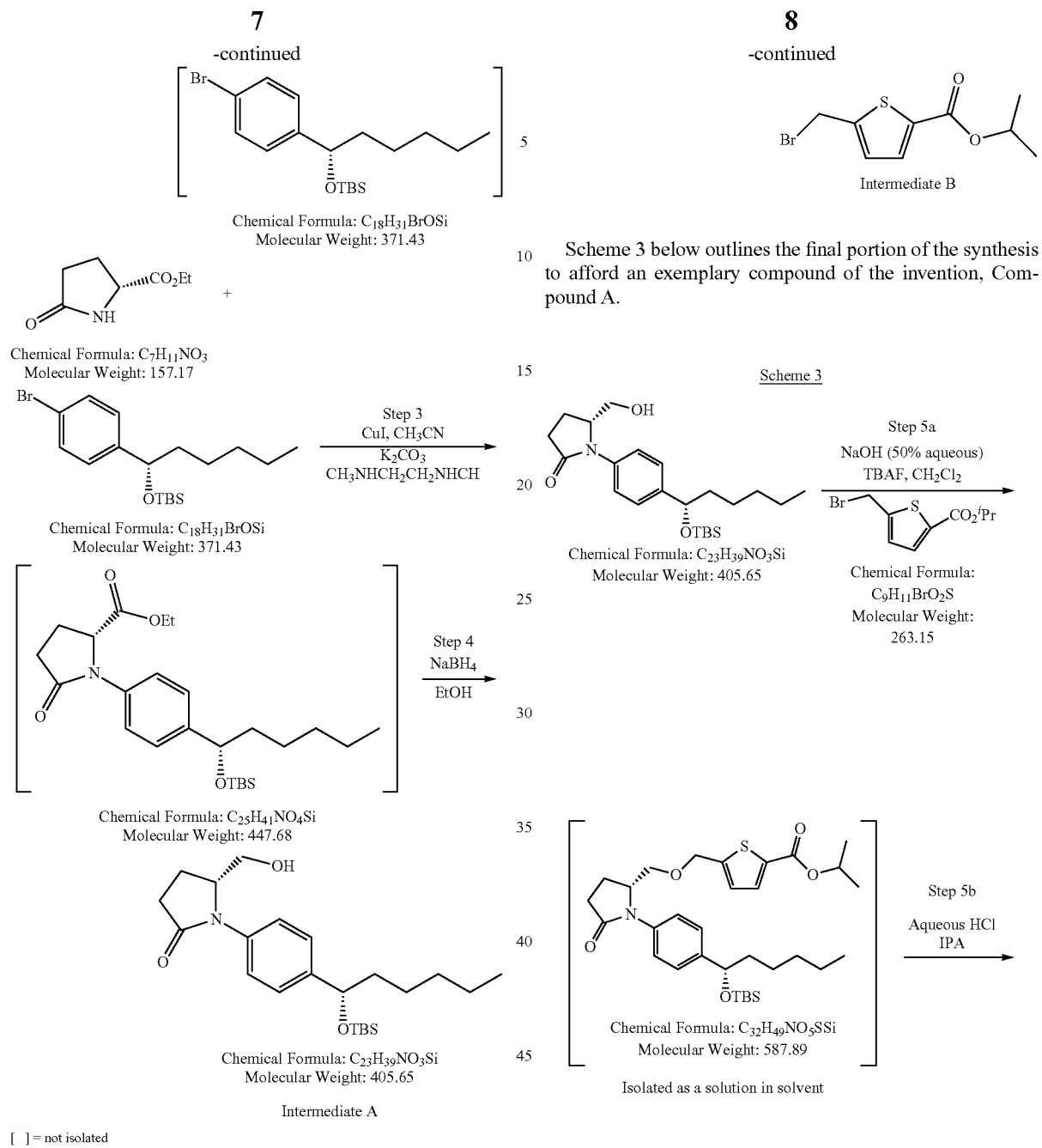
Scheme 3 below outlines the final portion of the synthesis to afford an exemplary compound of the invention, Compound A.
An exemplary synthetic route to Intermediate B is outlined below in Scheme 2.
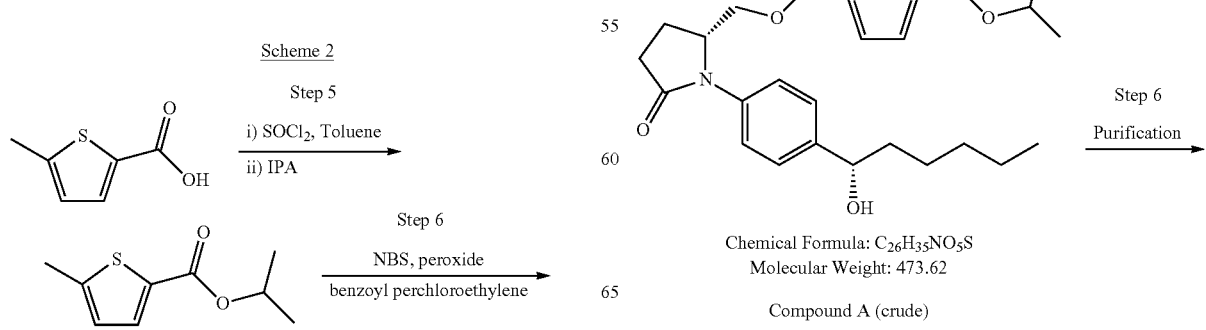

-continued

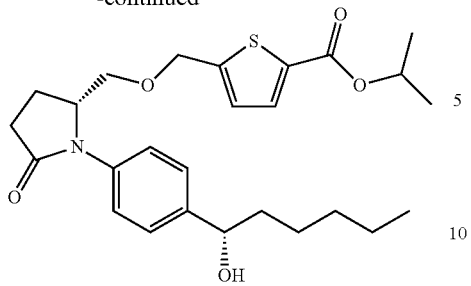

Chemical Formula: C$_{26}$H$_{35}$NO$_5$S
Molecular Weight: 473.62

Compound A

[ ] = not isolated

The following examples are intended only to illustrate the invention and should in no way be construed as limiting the invention.

EXAMPLES

Synthesis of (R)-5-Oxo-pyrrolidine-2-carboxylic acid ethyl ester

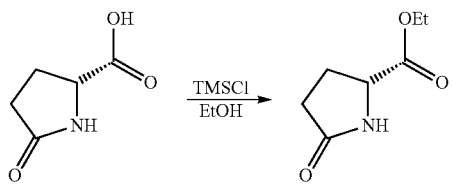

To a flask containing anhydrous ethanol and D-pyroglutamic acid at ambient temperature (~23° C.) was slowly added trimethylsilyl chloride while maintaining a reaction temperature NMT 30° C. After stirring at ambient temperature for a period of time, the reaction solution was concentrated under reduced pressure to give a yellow oil. The product was dissolved in toluene and concentrated under reduced pressure to give a yellow oil. The crude product was dissolved in dichloromethane and stirred with the slow addition of aqueous saturated sodium bicarbonate solution until a pH of 7-8 was reached. The organic layer was isolated, and the aqueous layer was extracted further with dichloromethane. The combined organic layers were dried over sodium sulfate, filtered and concentrated under reduced pressure to give product, (R)-5-oxo-pyrrolidine-2-carboxylic acid ethyl ester, as a yellow oil.

Synthesis of [(S)-1-(4-Bromo-phenyl)-hexyloxy]-tert-butyl-dimethyl-silane

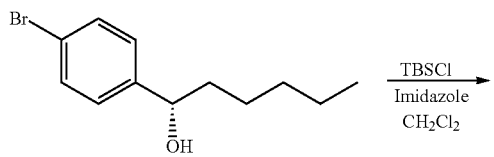

-continued

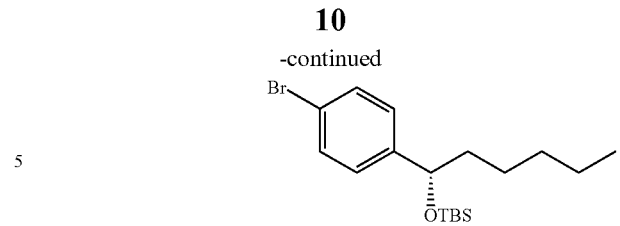

To a flask containing (S)-1-(4-Bromo-phenyl)-hexan-1-ol in CH$_2$Cl$_2$ at ambient temperature (~23° C.) was added imidazole and t-butyldimethylsilyl chloride. The reaction mixture was stirred at ambient temperature for a period of time until all starting material was consumed before quenching with a mixture of MeOH and water. The organic layer was washed with deionized water and concentrated under reduced pressure to give the product as a yellow oil.

Synthesis of (R)-ethyl 1-(4-((S)-1-(tert-butyldimethylsilyloxy)hexyl)phenyl)-5-oxopyrrolidine-2-carboxylate

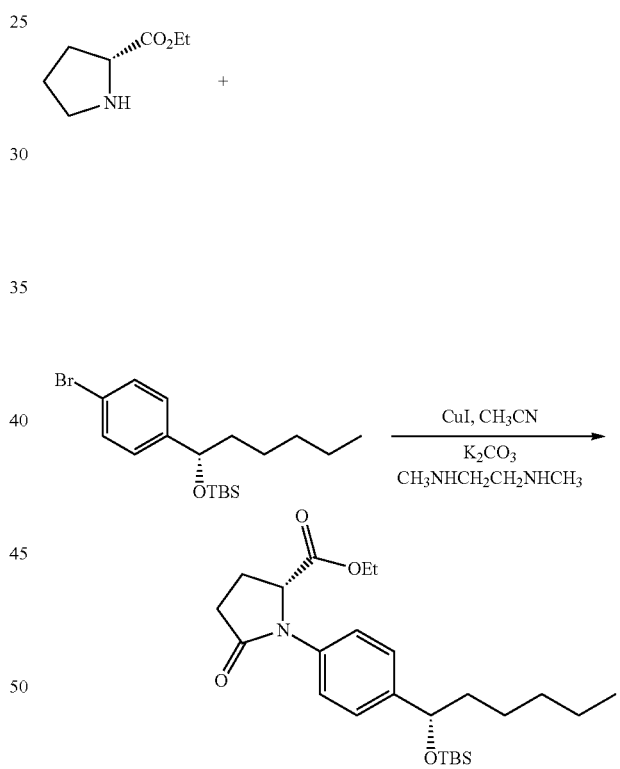

To a flask containing acetonitrile was added [(S)-1-(4-bromo-phenyl)-hexyloxy]-tert-butyl-dimethyl-silane and potassium carbonate. The solution mixture was heated to reflux for a period of time. The solution mixture was then cooled to ambient temperature (~23° C.) before adding a solution of (R)-5-oxo-pyrrolidine-2-carboxylic acid ethyl ester in acetonitrile, CuI and N,N'-dimethylethylenediamine. The reaction mixture was heated to reflux until the ethyl ester was consumed. The reaction mixture was cooled to ambient temperature, filtered through a bed of Celite and rinsed forward with acetonitrile. The filtrate was washed twice with aqueous ammonium acetate and dried over sodium sulfate.

The mixture was passed through a bed of silica, washed with MTBE, and concentrated under reduced pressure to give the product as a light yellow oil.

Synthesis of (R)-1-{4-[(S)-1-(tert-Butyl-dimethyl-silanyloxy)-hexyl]-phenyl}-5-hydroxymethyl-pyrrolidin-2-one

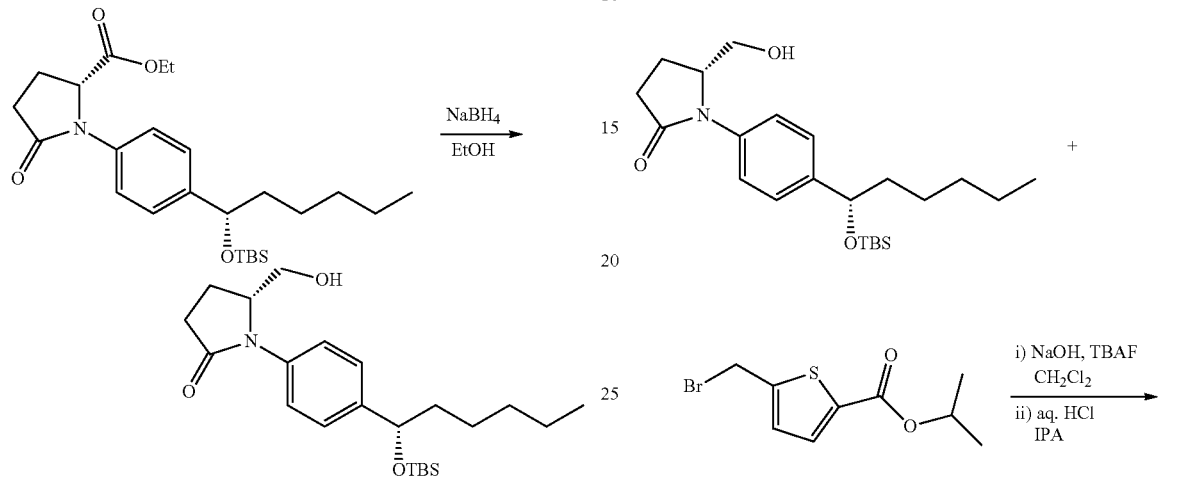

To a flask containing ethanol and (R)-1-{4-[(S)-1-(tert-butyl-dimethyl-silanyloxy)-hexyl]-phenyl}-5-oxo-pyrrolidine-2-carboxylic acid ethyl ester was added aqueous potassium phosphate bibasic followed by an aqueous solution of sodium borohydride, while maintaining the reaction at ambient temperature (~23° C.). The mixture was stirred at ambient temperature until all of the ethyl ester was consumed before quenching with water, and then extracted with MTBE. The combined organic extracts were washed with brine and concentrated under reduced pressure to give crude product as an off-white solid. The crude product was re-crystallized with heptanes to give a pure product.

Synthesis of isopropyl 5-(bromomethyl)thiophene-2-carboxylate

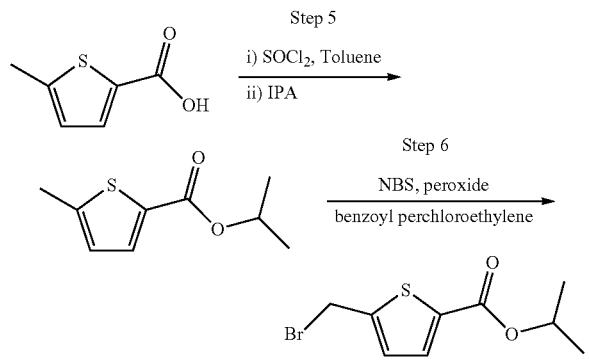

Step 5 involves converting the commercially available starting material 5-methylthiophene-2-carboxylic acid to its isopropyl 5-methylthiophene-2-carboxylate making the acid chloride in situ and then reacting it with IPA. Step 6 converts 5-methylthiophene-2-carboxylate to isopropyl 5-(bromomethyl)thiophene-2-carboxylate by radical reaction with NBS (N-bromosuccinimide) and peroxide in perchloroethylene followed by re-crystallization from heptane to yield pure the product.

Synthesis of 5-{(R)-1-[4-((S)-1-Hydroxy-hexyl)-phenyl]-5-oxo-pyrrolidin-2-ylmethoxymethyl}-thiophene-2-carboxylic acid isopropyl ester (crude)

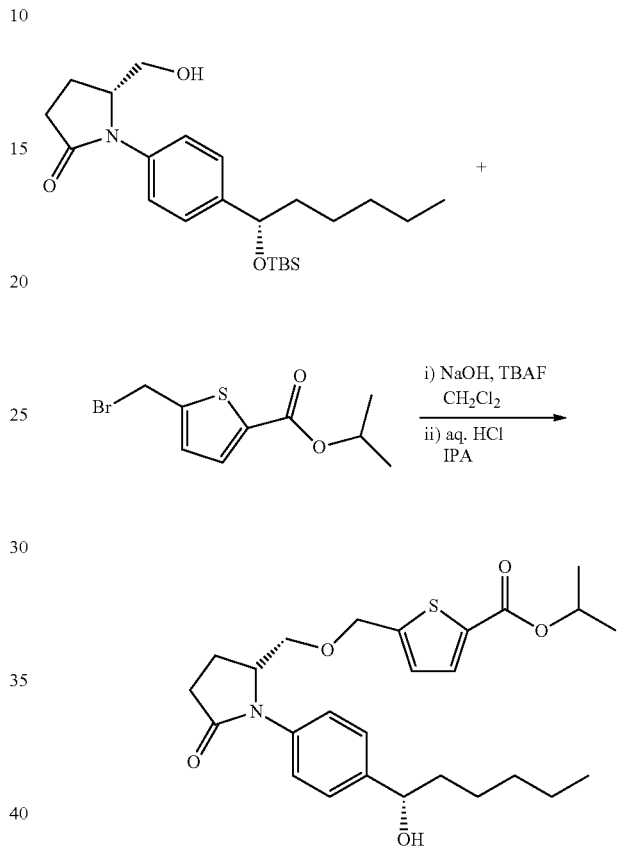

To a flask containing a mixture of (R)-1-{4-[(S)-1-(tert-butyl-dimethyl-silanyloxy)-hexyl]-phenyl}-5-hydroxymethyl-pyrrolidin-2-one and isopropyl 5-(bromomethyl)thiophene-2-carboxylate in $CH_2Cl_2$ at ambient temperature (~23° C.) was slowly added a 50% aqueous NaOH solution and followed by TBAB. The reaction mixture was stirred at ambient temperature for a period of time until (R)-1-{4-[(S)-1-(tert-butyl-dimethyl-silanyloxy)-hexyl]-phenyl}-5-hydroxymethyl-pyrrolidin-2-one was consumed. Carbon dioxide was then bubbled into the stirred biphasic reaction mixture until pH of the aqueous layer reached NMT 7. The stirring was stopped and the reaction mixture was allowed to separate into aqueous and organic layers. The aqueous layer was washed with DCM a few times. The DCM washes were combined with the organic layer and concentrated in vacuum until dryness to afford crude product. The crude product was then dissolved in isopropyl alcohol and stirred at ambient temperature (~23° C.) until the solution became homogeneous. The reaction solution was added with aqueous hydrochloric acid and stirred at ambient temperature (~23° C.) for a period of time until HPLC analysis indicated no more starting material remained. MTBE was added to the reaction solution. The solution mixture was then washed with an aqueous solution of sodium bicarbonate and brine solution before being concentrated under reduced pressure to give the crude product as a yellow to amber oil.

Purification of 5-{(R)-1-[4-((S)-1-Hydroxy-hexyl)-phenyl]-5-oxo-pyrrolidin-2-ylmethoxymethyl}-thiophene-2-carboxylic acid isopropyl ester

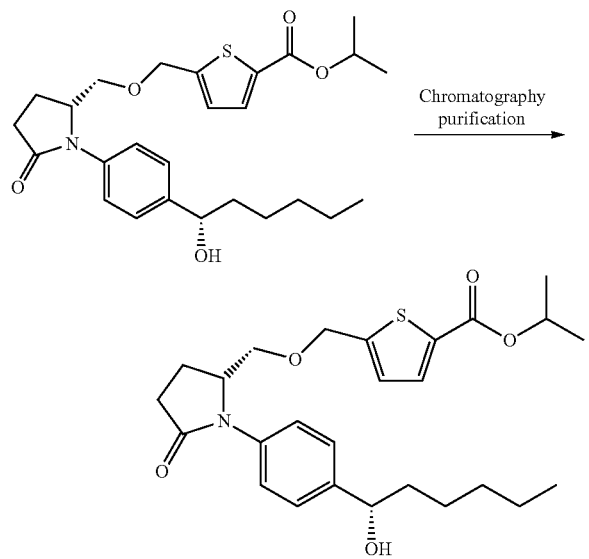

The crude 5-{(R)-1-[4-((S)-1-hydroxy-hexyl)-phenyl]-5-oxo-pyrrolidin-2-ylmethoxymethyl}-thiophene-2-carboxylic acid isopropyl ester was dissolved into MTBE then loaded onto a column of silica gel and eluted with gradient MTBE in n-heptanes. Fractions containing the crude product (>98% (a/a) by HPLC) were combined and concentrated under reduced pressure to give a yellow oil. The product was then dissolved in IPA, passed through a capsule-polishing filter, and then concentrated under reduced pressure at NMT 40° C. to give pure product as a yellow to amber oil.

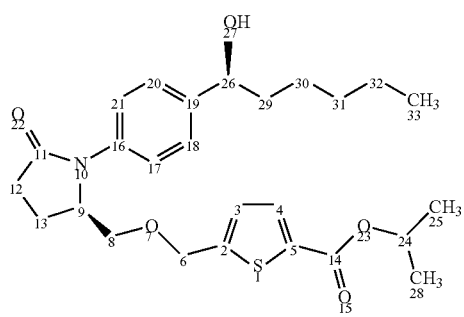

TABLE 1

| Chemical Shift assignments for Compound A[1,2] | | |
|---|---|---|
| Atom Number | Carbon | Proton |
| 2 | 148.80 | — |
| 3 | 126.62 | 6.98 (d, 1H, J = 3.76 Hz) |
| 4 | 133.05 | 7.59 (d, 1H, J = 3.76 Hz) |
| 5 | 132.88 | — |
| 6 | 67.03 | 4.60 (m, 2H) |

TABLE 1-continued

| Chemical Shift assignments for Compound A[1,2] | | |
|---|---|---|
| Atom Number | Carbon | Proton |
| 8 | 69.71 | 3.46 (d, 2H, J = 3.76 Hz) |
| 9 | 58.50 | 4.44 (m, 1H, o) |
| 11 | 173.71 | — |
| 12 | 31.02 | 2.35 (m, 1H) |
| | | 2.56 (ddd, 1H, J = 16.76, 9.79, 8.31 Hz) |
| 13 | 21.13 | 1.98 (m, 1H) |
| | | 2.24 (m, 1H) |
| 14 | 160.82 | — |
| 16 | 136.13 | — |
| 17, 21 | 123.13 | 7.36 (d, 2H, J = 8.51 Hz) |
| 18, 20 | 126.00 | 7.28 (d, 2H, J = 8.51 Hz) |
| 19 | 143.38 | — |
| 24 | 68.49 | 5.08 (m, 1H, o) |
| 25, 28 | 21.61 | 1.30 (d, 2H, J = 6.31 Hz) |
| 26 | 71.81 | 4.47 (m, 1H, o) |
| 27 | — | 5.06 (d, 2H, J = 4.55 Hz, o) |
| 29 | 39.17 (o) | 1.56 (m, 2H) |
| 30 | 24.20 | 1.20 (m, 1H, o) |
| | | 1.33 (m, 1H, o) |
| 31 | 31.20 | 1.23 (m, 2H, o) |
| 32 | 22.07 | 1.23 (m, 2H, o) |
| 33 | 13.88 | 0.83 (m, 3H) |

[1]DMSO-$d_6$, 26° C. Protons referenced to DMSO-$d_6$. Carbons referenced to DMSO-$d_6$.
[2]Standard abbreviations: s = singlet; d = doublet; t = triplet; q = quartet; qui = quintet; m = multiplet; br = broad; o = overlapped (too overlapped for integration and\or multiplicity determination)

While this invention has been described with respect to these specific examples, it is understood that other modifications and variations are possible without departing from the spirit of the invention.

What is claimed is:

1. A process for preparing a compound having the general structure (1)

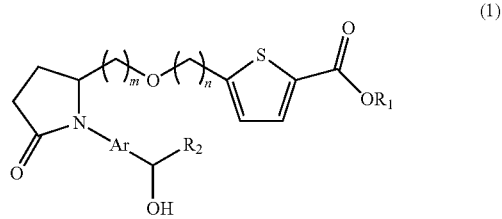

wherein:
$R_1$ is H, $C_1$-$C_6$ alkyl, or hydroxyethyl;
$R_2$ is $C_1$-$C_{10}$ alkyl;
Ar is $C_5$-$C_{10}$ arylene or heteroarylene; and
m and n are each independently 1-6;
comprising:
a) reacting compound (2)

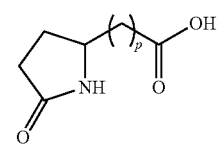

wherein p is 0 to 5;
with an alcohol having the structure $R_1$—OH under suitable esterifying conditions to provide compound (3)

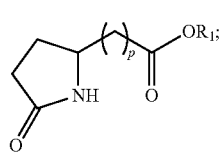
(3)

(b) coupling compound (3) with compound (5)

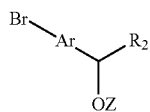
(5)

wherein Z is a protecting group,
under suitable conditions to provide compound (6)

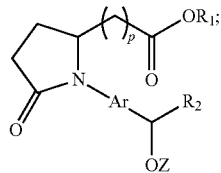
(6)

(c) subjecting compound (6) to sufficient reducing conditions to provide compound (7)

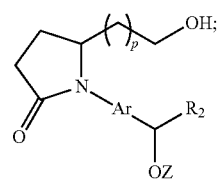
(7)

(d) coupling compound (7) with compound (8)

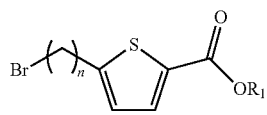
(8)

under suitable conditions to provide compound (9)

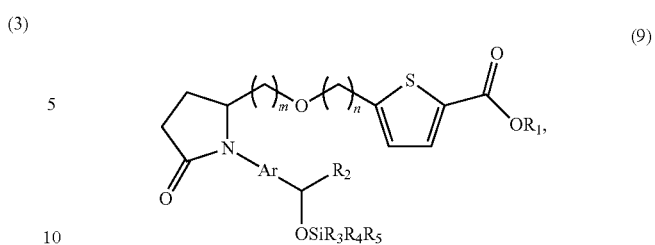
(9)

wherein $R_3$, $R_4$ and $R_5$ are each independently $C_1$-$C_4$ straight or branched chain alkyl; and (e) subjecting compound (9) to acidifying conditions,
thereby providing a compound of general structure (1).

2. The process of claim 1, wherein Ar is phenylene or naphthylene.

3. The process of claim 1, wherein Ar is phenylene.

4. The process of claim 1 wherein $R_1$ is $C_3$ alkyl.

5. The process of claim 1 wherein $R_1$ is isopropyl.

6. The process of claim 1 wherein $R_2$ is linear $C_5$ alkyl.

7. The process of claim 1 wherein m and n are 1.

8. The process of claim 1, wherein coupling step (b) is performed in the presence of a metal halide catalyst.

9. The process of claim 8 wherein the catalyst is a copper halide.

10. The process of claim 8 wherein the catalyst is CuI.

11. The process of claim 1 wherein the compound (I) has the structure:

Compound A

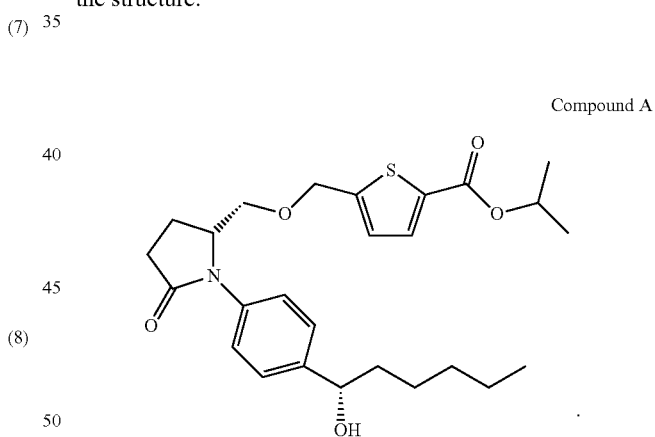

* * * * *